(12) United States Patent
Horns

(10) Patent No.: US 7,034,155 B2
(45) Date of Patent: Apr. 25, 2006

(54) METHOD FOR PRODUCING N-ETHYL-N-[3-(3-CYANOPYRAZOLO[1,5A]PYRIMIDINE-7-YL)PHENYL]ACETAMIDE

(75) Inventor: Stefan Horns, Schaffhausen (CH)

(73) Assignee: Cilag AG, Schaffhausen (CH)

( * ) Notice: Subject to any disclaimer, the term of this patent is extended or adjusted under 35 U.S.C. 154(b) by 0 days.

(21) Appl. No.: 10/504,561

(22) PCT Filed: Jan. 17, 2003

(86) PCT No.: PCT/CH03/00026

§ 371 (c)(1),
(2), (4) Date: Mar. 18, 2005

(87) PCT Pub. No.: WO03/068775

PCT Pub. Date: Aug. 21, 2003

(65) Prior Publication Data

US 2005/0171349 A1    Aug. 4, 2005

(30) Foreign Application Priority Data

Feb. 14, 2002   (CH) .......................... 2002 0250/02

(51) Int. Cl.
*C07D 487/04*   (2006.01)

(52) U.S. Cl. .................................................... 544/281
(58) Field of Classification Search ................. 544/281
See application file for complete search history.

(56) References Cited

U.S. PATENT DOCUMENTS 4,626,538 A * 12/1986 Dusza et al. ............. 514/259.1

FOREIGN PATENT DOCUMENTS

EP          0776898 A      6/1997

* cited by examiner

*Primary Examiner*—Thomas C. McKenzie
(74) *Attorney, Agent, or Firm*—Hoffmann & Baron, LLP

(57) ABSTRACT

N-ethyl-N-[3-(3-cyanopyrazolo[1,5-a]pyrimidine-7-yl)phenyl]acetamide (Zaleplon) can be produced by condensing 3-(N-acetyl-N-ethyl-amino)-β-oxo-phenylpropanal sodium salt with 3-amino-4-cyanopyrazole. Said sodium salt can be produced by first treating 3-acetylamino-acetophenone with an alkali metal hydroxide, in particular with powdered potassium hydroxide and then with an ethylating reagent, in particular ethyl bromide and the N-(3-acetylphenyl)-N-ethyl-acetamide that is obtained is reacted with a formic acid alkyl ester in the presence of an alkali metal alkanolate, in particular in the presence of sodium ethanolate. Zaleplon is the active ingredient of the soporific licensed under the trade name Sonata®.

10 Claims, No Drawings

METHOD FOR PRODUCING N-ETHYL-N-[3-(3-CYANOPYRAZOLO[1,5A]PYRIMIDINE-7-YL)PHENYL]ACETAMIDE

CROSS-REFERENCE TO RELATED APPLICATIONS

This application is the National Stage of International Application No. PCT/CH03/00026, filed Jan. 17, 2003, which claims the benefit of Swiss Application No. 0250/02, filed Feb. 14, 2002, the contents of which is incorporated by reference herein.

The present invention relates to a novel process for the preparation of N-ethyl-N-[3-(3-cyanopyrazolo[1,5-a]pyrimidin-7-yl)phenyl]acetamide of formula III:

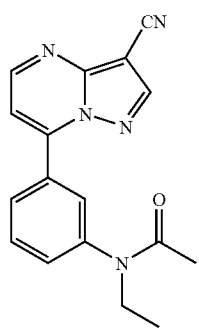

III

This is the active ingredient of the hypnotic authorized under the trade name Sonata®.

The process according to the invention is characterized in that the sodium salt of 3-(N-acetyl-N-ethylamino)-β-oxophenylpropanal of formula I:

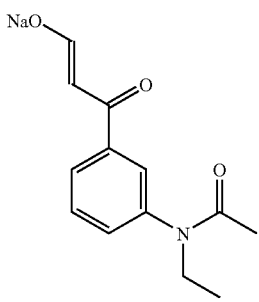

I is condensed with 3-amino-4-cyanopyrazole of formula II:

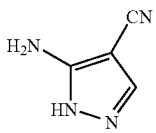

II

This condensation reaction is conveniently carried out in a mixture of glacial acetic acid, ethanol, isopropanol, acetone or tetrahydrofuran with concentrated hydrochloric acid and water. The reaction medium comprises preferably about 150 to 500, particularly preferably about 300 to 400 and very particularly preferably about 340 parts by weight of glacial acetic acid, ethanol, isopropanol, acetone or tetrahydrofuran, about 30 to 100, particularly preferably about 45 to 55 and very particularly preferably about 50 parts by weight of concentrated (i.e. approx. 37%) hydrochloric acid and about 100 to 400, particularly preferably about 250 to 300 and very particularly preferably about 270 parts by weight of water. A particularly preferred reaction medium is a mixture of glacial acetic acid with concentrated hydrochloric acid and water, especially a mixture comprising about 150 to 500, particularly preferably about 300 to 400 and very particularly preferably about 340 parts by weight of glacial acetic acid, about 30 to 100, particularly preferably about 45 to 55 and very particularly preferably about 50 parts by weight of concentrated (i.e. approx. 37%) hydrochloric acid and about 100 to 400, particularly preferably about 250 to 300 and very particularly preferably about 270 parts by weight of water. By way of example, in one possible procedure, about 30 parts by weight of the compound of formula II are placed in about 340 parts by weight of glacial acetic acid, about 50 parts by weight of concentrated, i.e. approx. 37%, hydrochloric acid are added at room temperature, then, after cooling to about 5 to 10° C., especially to about 7° C., a solution of about 70 parts by weight of the sodium salt of formula I in about 270 parts by weight of water is slowly added dropwise, conveniently over about one hour, and the mixture is then stirred for some time, especially for about one hour, with cooling at around the temperature mentioned above. About 150 to 800, conveniently about 300 to 500 and preferably about 400 parts by weight of water are then added, after which the product can be filtered off, washed with water (conveniently twice with about 150 parts by weight of water each time) and dried, conveniently under vacuum at about 50 to 80° C., especially at about 60 to 70° C. The compound of formula III, i.e. zaleplon, can thus be obtained in good yield and purity in the form of a white solid.

The sodium salt of formula I above, used as the starting material, can be prepared according to the invention by treating 3-acetylaminoacetophenone of formula IV:

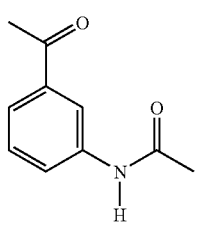

IV firstly with an alkali metal hydroxide and then with an ethylating agent, and then reacting the resulting N-(3-acetylphenyl)-N-ethylacetamide of formula VII:

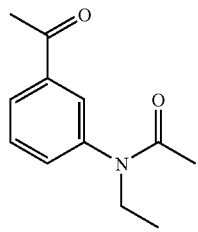

VII with an alkyl formate in the presence of an alkali metal alcoholate.

The alkali metal hydroxide used in the first of these two stages is conveniently potassium hydroxide, preferably powdered solid potassium hydroxide, and the ethylating agent used in conveniently ethyl bromide. This ethylation is preferably carried out in tetrahydrofuran. By way of example, in one possible procedure, about 100 parts by weight of 3-acetylaminoacetophenone of formula IV and about 45 to 100 parts by weight, preferably about 65 parts by weight, of powdered potassium hydroxide are dissolved in about 200 to 500 parts by weight, preferably about 350 parts by weight, of anhydrous tetrahydrofuran under an inert gas atmosphere, conveniently under a nitrogen atmosphere, and with stirring, and about 100 to 250 parts by weight, preferably about 155 parts by weight, of ethyl bromide, optionally diluted with tetrahydrofuran, are then added at about 35 to 50° C., preferably at about 40 to 45° C. After a number of hours, conveniently about 2 to 15 hours and preferably about 5 to 6 hours, the mixture can be cooled to room temperature and neutralized with aqueous acid, conveniently with dilute hydrochloric acid; the organic phase can then be separated off and concentrated to dryness, after which the residue can be dried e.g. by distilling off the remaining moisture azeotropically by means of toluene or the like. The compound of formula VII is obtained in high yield (around 95%) and satisfactory purity (about 80 to 92%) in the form of an oil.

In the second of the two stages of the preparation of the sodium salt of formula I, the alkali metal alkanolate and alkyl formate used are conveniently sodium ethylate and ethyl formate respectively. Again the reaction is conveniently carried out in tetrahydrofuran. By way of example, in one possible procedure, about 60 to 65 parts by weight of the oil obtained in the first stage (content about 80 to 92%) are dissolved in about 120 to 400 parts by weight, preferably about 200 to 250 parts by weight, of anhydrous tetrahydrofuran, after which about 25 to 80 parts by weight, preferably about 35 to 40 parts by weight, of ethyl formate and about 120 to 300 parts by weight, preferably about 160 to 170 parts by weight, of an approximately 20 to 25% solution of sodium ethanolate in ethanol are added at room temperature, with stirring. After stirring at room temperature for some hours, conveniently about 1 to 24 hours and preferably about 4 to 6 hours, further tetrahydrofuran can optionally be added to the reaction mixture, and the precipitated product, i.e. the sodium salt of formula I, can be filtered off, washed (e.g. twice with about 45 parts by weight of tetrahydrofuran each time) and then dried, conveniently under vacuum at about 40 to 50° C. The sodium salt of formula I can thus be obtained in good yield in the form of a non-hygroscopic powder.

EP 0 208 864 B1 and U.S. Pat. No. 4,626,538 A describe that zaleplon of formula III above can be prepared by converting 3-acetylaminoacetophenone of formula IV above into N-[3-(3-dimethylamino)-1-oxo-2-propenyl)phenyl]acetamide of formula V:

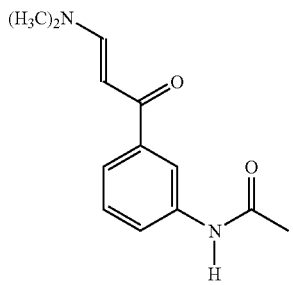

V by reaction with N,N-dimethylformamide dimethylacetal, converting the compound V into the corresponding N-ethyl compound of formula VI:

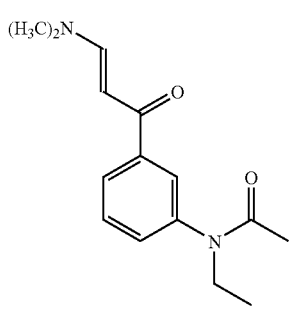

VI with an ethyl halide (e.g. ethyl bromide or iodide), in the presence of sodium hydride, and condensing the compound VI with 3-amino-4-cyanopyrazole of formula II above, under reflux in glacial acetic acid; in a variant of this process, it is also possible to condense N-[3-(3-dimethylamino)-1-oxo-2-propenyl)phenyl]-acetamide of formula V above with 3-amino-4-cyanopyrazole of formula II above and then to ethylate the resulting product. According to EP 0 776 898 A1 and U.S. Pat. No. 5,714,607 A, zaleplon is obtained as a purer and more easily isolatable product by carrying out the condensation reaction of the compounds of formulae VI and II above in a mixture of water and acetic acid rather than in glacial acetic acid, the proportion of water being conveniently about 10 to 85%, preferably about 11 to 75% and especially 60 to 75%.

Like the known processes discussed above, the process according to the invention is also ultimately based on 3-acetylaminoacetophenone if one takes into account the precursors according to the invention that yield the sodium salt of formula I above. However, compared with these known processes, the process according to the invention offers the following substantial advantages:

In the ethylation (IV⇒VII compared with V⇒VI), potassium hydroxide is used instead of sodium hydride, which is considerably more expensive and carries high safety risks.

Instead of N,N-dimethylformamide dimethylacetal (IV⇒V) it is possible to use ethyl formate/sodium ethanolate (VII⇒I), which are substantially better value for money and are available on a larger scale.

The sodium salt of formula I can be isolated very easily as it separates out of the reaction mixture directly in high yield and purity and can simply be filtered off.

Whereas zaleplon of formula III obtained by condensing the compounds of formulae VI and II in aqueous glacial acetic acid (cf. EP 0 776 898 A1 and U.S. Pat. No. 5,714,607 A) is contaminated, after work-up, with around 1%, i.e. about 0.8 to 1.3%, of an isomer (forming in an amount of about 3 to 6% in the reaction mixture), requiring an expensive purification, the condensation reaction according to the invention between the compounds of formulae I and II, especially under the preferred reaction conditions described earlier, and specifically under the conditions described in Example 2 below, succeeds in minimizing this by-product to less than 0.1%.

The Examples which follow will illustrate the present invention in greater detail without in any way limiting its scope.

EXAMPLE 1 a) Synthesis of N-(3-acetylphenyl)-N-ethylacetamide (VII)

100 g (0.564 mol) of 3-acetylaminoacetophenone and then 63.2 g (1.13 mol) of powdered potassium hydroxide are dissolved in anhydrous THF (350 g) under an $N_2$ atmosphere, with stirring, and a solution of 154 g (1.41 mol) of ethyl bromide in anhydrous THF (180 g) is added at 40–45° C.

After 5–6 h the mixture is cooled to room temperature and neutralized by the addition of 192.5 g (0.39 mol) of 2 M HCl and 45 g of water. The organic phase is separated off and concentrated to dryness and the residue is then co-distilled a further twice with 175 g of toluene.

This gives 133.4 g (content 82%, yield 94%) of the compound VII in the form of an oil.

b) Synthesis of the Na salt of 3-(N-acetyl-N-ethylamino)-β-oxophenylpropanal (I)

62.65 g (content 82%, 0.250 mol) of VII are dissolved in anhydrous THF (220 g), and 37.0 g (0.500 mol) of ethyl formate, followed by 162.1 g (0.500 mol) of a 21% solution of sodium ethanolate in ethanol, are then added at room temperature, with stirring.

After stirring for 4–6 h at room temperature, 220 g of THF are added and the precipitated product is then filtered off (on a suction filter), rinsed with twice 45 g of THF and dried under vacuum at 40–50° C.

This gives 61.16 g (85%) of the compound I in the form of a powder. The material is non-hygroscopic.

EXAMPLE 2

Synthesis of N-ethyl-N-(3-(3-cyanopyrazolo(1,5-a) pyrimidin-7-yl)phenyl)-acetamide (zaleplon) (III)

49.8 g (505 mmol) of 37% hydrochloric acid are added at room temperature to a solution of 30.0 g (275 mmol) of II in 340 g of glacial acetic acid, the mixture is cooled to 7° C. and a solution of 69.0 g (content 93%, 251 mmol) of I in 270 g of water is added dropwise over 1 h. After stirring for 1 h in the cold, 400 g of water are added and this is followed by filtration (on a suction filter) and washing with twice 150 g of water. The product is dried under vacuum at 60–70° C. to give 69.6 g (88%) of the compound III in the form of a white solid.

The invention claimed is:

1. A process for the preparation of N-ethyl-N-[3-(3-cyanopyrazolo[1,5-a]-pyrimidin-7-yl)phenyl]acetamide of formula III:

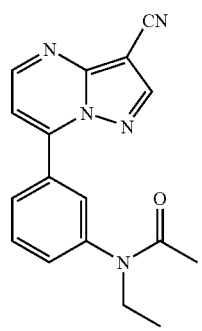

comprising the step of condensing the sodium salt of 3-(N-acetyl-N-ethylamino)-β-oxophenyl-propanal of formula I:

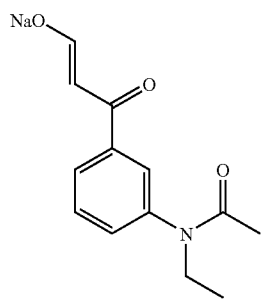

with 3-amino-4-cyanopyrazole of formula II:

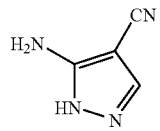

2. The process of claim 1, wherein the condensation reaction is carried out in a reaction medium comprising a mixture of:
   a. a solvent selected from the group consisting of glacial acetic acid, ethanol, isopropanol, acetone, and tetrahydrofuran;
   b. concentrated hydrochloric acid; and
   c. water.

3. The process of claim 2 wherein,
   the solvent is of about 150 to about 500 parts by weight;
   the concentrated hydrochloric acid is of about 150 to about 500 parts by weight; and
   the water is of about 100 to about 400 parts by weight.

4. The process of claim 2, wherein the reaction medium comprises a mixture of:

a. glacial acetic acid;
b. concentrated hydrochloric acid; and
c. water.

5. The process of claim 4, wherein the reaction medium is mixture of about 150 to about 500 parts by weight of glacial acetic acid, about 30 to about 100 parts by weight of concentrated hydrochloric acid and about 100 to about 400 parts by weight by water.

6. The process of claim 1, wherein the starting material of formula I is prepared by the steps of:

1. treating 3-acetylaminoacetephenone of formula IV:

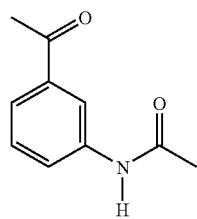

firstly with an alkali metal hydroxide and then with an ethylating agent, and 2. reacting the resulting N-(-3-acetylphenyl)-N-ethylacetamide of formula VII:

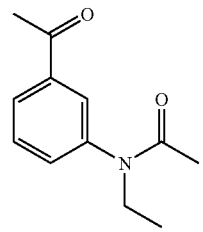

with an alkyl formate in the presence of an alkali metal alkanolate.

7. The process of claim 6, wherein the alkali metal hydroxide of step 1 is postassium hydroxide and the ethylating agent of step 1 is ethyl bromide.

8. The process of claim 7, wherein the ethylation of step 1 is carried out in tetrahydrofuran.

9. The process of claim 6, wherein the alkali metal alkanoate of step 2 is sodium ethylate.

10. The process of claim 9, wherein the reaction is carried out in tetrahydrofuran.

* * * * *